United States Patent [19]

Archibald et al.

[11] 4,209,521
[45] Jun. 24, 1980

[54] ANTI-DEPRESSANT INDOLE DERIVATIVES

[75] Inventors: John L. Archibald, Windsor; Terence J. Ward, Slough, both of England

[73] Assignee: John Wyeth & Brother Limited, Maidenhead, England

[21] Appl. No.: 958,763

[22] Filed: Nov. 8, 1978

[30] Foreign Application Priority Data

Dec. 1, 1977 [GB] United Kingdom ............... 50053/77

[51] Int. Cl.² ................. A61K 31/445; C07D 401/06; C07D 409/14
[52] U.S. Cl. .................... 424/267; 546/201; 546/212; 546/224; 546/273
[58] Field of Search ........... 546/201; 424/267

[56] References Cited

U.S. PATENT DOCUMENTS

| 4,061,641 | 12/1977 | Archibald et al. | 546/201 |
| 4,073,911 | 2/1978 | Huebner | 546/196 X |

FOREIGN PATENT DOCUMENTS 1425354 2/1976 United Kingdom ..................... 546/201

*Primary Examiner*—Henry R. Jiles
*Assistant Examiner*—Richard A. Schwartz
*Attorney, Agent, or Firm*—Arthur E. Wilfond

[57] ABSTRACT

The invention concerns a compound of formula II

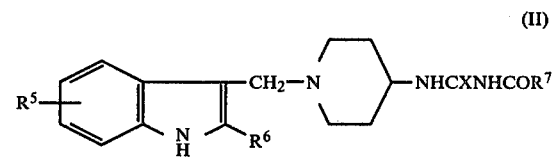

or a pharmaceutically acceptable acid addition or quaternary ammonium salt thereof wherein $R^5$ represents hydrogen, hydroxy, lower alkoxy or lower alkyl, $R^6$ represents hydrogen or lower alkyl, and $R^7$ represents phenyl, lower alkoxy phenyl, halophenyl, or thenyl and X represents oxygen or sulphur. These indole derivatives exhibit psychotropic activity. The invention includes a method of alleviating depression in a warm blooded animal afflicted with depression which method comprises administering to said animal an effective amount of a compound of formula II or a pharmaceutically acceptable acid addition salt thereof.

5 Claims, No Drawings

ANTI-DEPRESSANT INDOLE DERIVATIVES

The invention relates to new indole derivatives to processes for preparing them and to pharmaceutical compositions containing them. In United Kingdom patent specification No. 1,425,354, which corresponds to U.S. Application Ser. No. 597,841, filed July 21, 1975, of Archibald et al, is described and claimed compounds of the general formula:

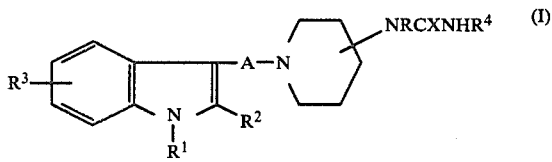

and acid addition and quaternary ammonium salts thereof, wherein R represents hydrogen or lower alkyl, $R^1$ represents hydrogen, lower alkyl, aryl lower alkyl or aroyl, $R^2$ represents hydrogen, lower alkyl, or aryl, $R^3$ represents hydrogen, halogen, lower alkoxy, aryl lower alkoxy, hydroxy or lower alkyl, $R^4$ represents hydrogen, lower alkyl, cycloalkyl of 5 to 7 carbon atoms, aryl lower alkyl, aryl (including heterocyclic aryl), or acyl, A represents an alkylene, mono- or dioxo- or hydroxyalkylene radical having from 1 to 5 carbon atoms and X represents oxygen or sulphur.

According to U.K. patent specification No. 1,425,354 the compounds of formula I exhibit action on the cardiovascular system, particularly hypotensive and/or anti-hypertensive activity. We have now surprisingly found that certain compounds falling within the general formula I, but not exemplified in said U.K. specification, exhibit psychotropic activity as measured by inhibition of uptake of 5-hydroxytryptamine in brain slices, while possessing much reduced hypotensive or anti-hypertensive activity as compared to other compounds of the general formula I. The compounds are therefore of value as antidepressants. The present invention therefore concerns these compounds and their use.

The present invention therefore provides new compounds of formula II

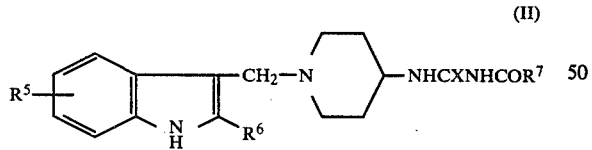

and pharmaceutically acceptable acid addition and quaternary ammonium salts thereof wherein $R^5$ represents hydrogen, hydroxy, lower alkoxy or lower alkyl, $R^6$ represents hydrogen or lower alkyl, and $R^7$ represents phenyl, lower alkoxy phenyl, halophenyl, or thenyl and X represents oxygen or sulphur.

The term "lower" in relation to alkyl and alkoxy radicals used herein means that the radical contains from 1 to 6 carbon atoms. Usually such radicals containing from 1 to 4 carbon atoms are preferred.

Examples of lower alkyl radicals for $R^5$ or $R^6$ are methyl, ethyl, n-propyl, iso-propyl, n-butyl and iso-butyl. Examples of lower alkoxy radicals for $R^5$ are methoxy, ethoxy, propoxy and butoxy. When $R^5$ is hydroxy or lower alkoxy this is preferably in the 5-position.

The preferred compounds of the invention are 1-[1-(indol-3-ylmethyl)piperid-4-yl]-3-benzoyl urea; 1-benzoyl-3-[1-([5-hydroxyindol-3-yl]methyl)piperid-4-yl]urea; 1-[1-(indol-3-ylmethyl)piperid-4-yl]-3-(2-thenoyl)-urea and 1-[1-(indol-3-ylmethyl)piperid-4-yl]-3-benzoyl thiourea and their acid addition salts.

Processes for preparing compounds of formula II are included in the invention. The preferred process comprises reacting an indole of formula III

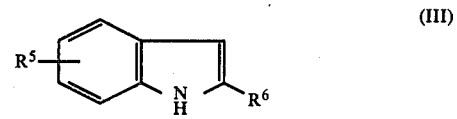

wherein $R^5$ and $R^6$ are as defined above with formaldehyde and a piperidine derivative of formula IV

wherein $R^7$ and X are as defined above.

The formaldehyde used in the above reactions may be in the form of a solution in an inert solvent or as paraformaldehyde.

Alternative methods of preparing compounds of formula II are as follows:

(i) acylation of a compound of formula V

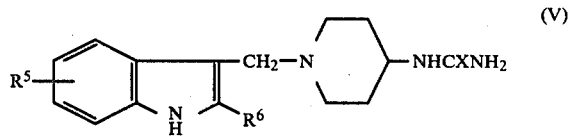

using an acylating agent containing the group $COR^7$;

(ii) reacting a compound of formula VI

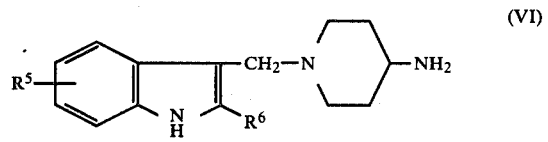

with an isocyanate or isothiocyanate of formula $R^7CONCX$ or with a compound of formula $R^7CONHCXNH_2$;

(iii) reacting a compound of formula VII

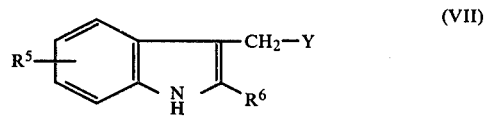

wherein Y is a halogen atom, or an equivalent replaceable atom or radical e.g. an organic sulphonyl radical such as a tosyl radical or a disubstituted amino radical such as dimethylamino or a trisubstituted ammonium radical such as trimethyl ammonium ($^{\oplus}NMe_3$), with a compound of formula IV as defined above;

(IV) reducing a compound of formula VIII or VIIIa

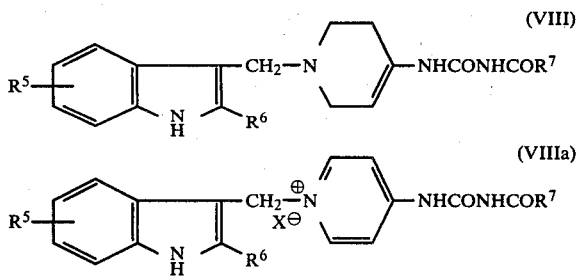

wherein $X^\ominus$ is an anion e.g. a halide ion, for example by catalytic hydrogenation e.g. in the presence of Raney nickel or a platinum catalyst;

(v) reacting a compound of formula IX

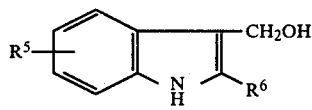

with a compound of formula IV as defined above where X is oxygen, in the presence of a catalyst e.g. Raney nickel.

In the above methods (i) to (v) $R^5$, $R^6$, $R^7$ and X are as previously defined.

When a compound of formula (I) is produced wherein $R^5$ represents lower alkoxy, dealkylation to the corresponding hydroxyl compound may be carried out in known manner. Methods of preparing the starting compounds of formula IV, V, VI, VII, VIIIa and IX are described generally in U.K. patent specification No. 1,425,354.

The invention also includes pharmaceutical compositions containing as active ingredient an active compound of formula II as above defined. The active compound may be finely comminuted if desired. In addition to the active ingredient, the compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxy-methyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid of solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

The following examples illustrate the invention.

EXAMPLE 1

1-[1-(Indol-3-ylmethyl)piperid-4-yl]-3-benzoylurea

Ice-cold 40% aqueous formaldehyde solution (0.62 cm$^3$, 0.0082 mole) was added to an ice-cooled solution of 4-benzoylureidopiperidine (2.00 g, 0.0081 mole) in water (8 cm$^3$) and acetic acid (2 cm$^3$). The solution was poured onto indole (0.95 g, 0.0081 mole), stirred for 16 hours at room temperature, and poured into a solution of potassium hydroxide (4.00 g) in water (40 cm$^3$). The solution and precipitated crystals were ice-cooled for 4 hours before collecting the crystals by filtration and washing them with ice-cold water (3×10 cm$^3$). The dried crystals were dissolved in the minimum quantity of ethanol and acidified (pH 1) with ethanolic hydrogen chloride. The solution was ice-cooled, on scratching and addition of ether, crystals were precipitated, which were collected by filtration, washed with ether (15 cm$^3$) and dried to give 1-[1-(indol-3-ylmethyl)piperid-4-yl]-3-benzoylurea as the hydrochloride three quarter hydrate (2.70 g, 81%) m.p. 261°–2° C.

$C_{22}H_{24}N_4O_2$ HCl. $\frac{3}{4}$ $H_2O$ requires C, 61.97; H, 6.26; N, 13.14 Found: C, 62.16; H, 6.10; N, 13.37.

EXAMPLE 2

1-[1-(5-Methoxyindol-3-ylmethyl)piperid-4-yl]-3-benzoylurea

Following the procedure of Example 1 but substituting 5-methoxy-indole for indole the title compound was obtained as the hydrochloride, three quarter hydrate mp 243°–246° C.

$C_{23}H_{26}N_4HCl \cdot \frac{3}{4} H_2O$ requires C, 60.52; H, 6.29; N, 12.27 Found: C, 60.83; H, 6.11; N, 12.35.

EXAMPLE 3

1-[1-(Indol-3-ylmethyl)piperid-4-yl]-3-(2-thenoyl)-urea

Following the procedure of Example 1, formaldehyde, 4-(2-thenoyl)ureidopiperidine and indole are reacted together to obtain the title compound which is isolated as the hydrochloride mp 231°–232° C.

EXAMPLE 4

1-Benzoyl-3-[1-([2-methylindol-3-yl]methyl)piperid-4-yl]urea

A solution of formaldehyde (1.6 cm$^3$, 40% aqueous solution) was added to a stirred solution of 4-benzoylureidopiperidine (5 g, 0.02 mol) and 2-methylindole (2.6 g, 0.02 mol) in acetic acid (12 cm$^3$). The solution was allowed to stand for 5 hours and diluted with water (100 cm$^3$). The precipitated solid was removed by filtration and discarded. The filtrate was basified by addition of ammonia to precipitate the product which was collected by filtration. The product was triturated with ethanol, then recrystallised from a mixture of acetonitrile (120 cm$^3$) and water (12 cm$^3$) to give the title compound as the pure base (1.65 g, 21%) m.p. 209°–11° C.

Found: C, 71.04; H, 6.78; N, 14.46; $C_{23}H_{26}N_4O_2$ requires C, 70.74; H, 6.71; N, 14.35%.

The base was suspended in methanol (15 cm$^3$) and acidified with ethanolic hydrogen chloride, on cooling in ice the crystalline hydrochloride of the title compound separated and was collected by filtration. Recrystallisation three times from methanol gave (0.55 g, 6.3%) m.p. 180°–81° C.(d). Found: C, 63.29; H, 6.37; N, 12.68; $C_{23}H_{26}N_4O_2$ HCl 0.5H$_2$O requires C, 63.37; H, 6.47; N, 12.85.

EXAMPLE 5

1-Benzoyl-3-[1-([5-hydroxyindol-3-yl]methyl)piperid-4-yl]urea

Formaldehyde (0.4 cm$^3$, 0.005 mol) was added to a stirred solution of 4-benzoylureidopiperidine (1.25 g, 0.005 mol) and 5-hydroxyindole (0.67 g, 0.005 mol) in acetic acid (3 cm$^3$). The solution was allowed to stand for 4 hours then diluted with water (50 cm$^3$). The precipitated solid was removed by filtration and the filtrate basified by addition of ammonia. The precipitated solid was collected by filtration, washed with water and recrystallised three times from methanol giving the title compound as the free base. The base was then suspended in ethanol (1 cm$^3$), acidified with ethanolic hydrogen chloride and isopropyl alcohol (1 cm$^3$) added to give a gummy solid which solidified on cooling and stirring to give the title compound as the hydrochloride hemihydrate (0.17 g, 8%) m.p. 200° C.

Found: C, 60.14; H, 6.11; N, 12.71; $C_{22}H_{24}N_4O_3 \cdot$ HCl 0.5H$_2$O requires C, 60.34; H, 5.98; N, 12.79.

EXAMPLE 6

3-(4-methoxybenzoyl)-1-(1-[indol-3-ylmethyl]piperid-4-yl)urea

Formaldehyde (0.4 cm$^3$, 40% aqueous solution) was added to a stirred solution of 4-(4-methoxybenzoylureido)piperidine (1.39 g, 0.005 mol) and indole (0.6 g, 0.005 mol) in acetic acid (3 cm$^3$). The solution was allowed to stand for 5 hours and the diluted with water (50 cm$^3$). The turbid solution was then basified by addition of ammonia solution and the precipitated solid collected by filtration washed with water and ether to give 2.1 g (95%) of the title compound as the free base. The base was suspended in warm ethanol (20 cm$^3$) and acidified with ethanolic hydrogen chloride. After stirring at room temperature for 1 hour and 0° C. for 0.5 hours the suspension was filtered to remove the hydrochloride. The hydrochloride was recrystallised from aqueous methanol (80% methanol, 20 cm$^3$) to give (1.8 g, 82%) of the hydrochloride of the title compound m.p. 220°–22° C.

Found: C, 62.27; H, 6.34; N, 12.35; $C_{23}H_{26}N_4O_3 \cdot$ HCl requires C, 62.37; H, 6.14; N, 12.65.

EXAMPLE 7

1-[1-(Indol-3-ylmethyl)piperid-4-yl]-3-(2-thenoyl)-urea 1-(Indol-3-ylmethyl)-4-ureidopiperidine (0.4 g, 1.47 mmol) was dissolved in a mixture of pyridine (10 ml) and dimethylformamide (4 ml) and thenyl-2-carbonyl chloride (0.27 g, 1.84 mmol) added. The solution was allowed to stand at room temperature for 5 days then further thenyl-2-carbonyl chloride (0.27 g, 1.84 mmol) was added. The next day the solvents were evaporated to give a deep red oil from which the title compound was precipitated as the hydrochloride by addition of methanol, m.p. 231°–232° C. (with slight decomposition).

Found: C, 56.78; H, 5.69; N, 13.67; $C_{20}H_{22}N_4O_2S \cdot$ HCl requires C, 57.34; H, 5.53; N, 13.37.

EXAMPLE 8

1-(4-Fluorobenzoyl)-3-(1-[indol-3-ylmethyl]piperid-4-yl)urea

Formaldehyde (0.4 cm$^3$, 40% aqueous solution) was added to a stirred solution of indole (0.6 g, 0.005 mol) and 4-(4-fluorobenzoylureido)piperidine (1.33 g, 0.005 mol) in acetic acid (3 cm$^3$). The reaction was allowed to stand for 5 hours then diluted with water (50 cm$^3$). The turbid solution was basified by addition of ammonia and the precipitated solid collected by filtration, washed with water and ether to give 1.7 g (85%) of the title compound as the free base. The base was suspended in ethanol (10 cm$^3$) and acidified with ethanolic hydrogen chloride. After stirring at room temperature for 0.5 hours and 0° C. for 0.5 hours the suspension was filtered to remove the hydrochloride. The hydrochloride was then dissolved in hot methanol acidified further with ethanolic hydrogen chloride and cooled to give the crystalline hydrochloride (1.4 g, 65.2%) double m.p. 210° C. and 260° C.

Found: C, 61.42; H, 5.76; N, 12.95. $C_{22}H_{23}FN_4O_2 \cdot$ HCl requires C, 61.32; H, 5.61; N, 13.00.

EXAMPLE 9

1-(Indol-3-ylmethyl)-4-ureidopiperidine

1-[1-(Indol-3-ylmethyl)piperid-4-yl]-3-benzoylurea (0.5 g, 1.33 mmol) was added to a solution of sodium hydroxide (1 g, 0.025 mol) in water (4 ml) and methanol (16 ml). The resulting suspension was stirred for 3 hours until all the solid material had dissolved then allowed to stand at room temperature overnight, giving a blue solution. The solvents were evaporated in vacuo and the solid residue triturated thoroughly with water, collected and dried (0.32 g, 88.9%). The obtained title compound was then recrystallised from aqueous ethanol, mp—softens slowly from 122°–128° C.

Found: C, 65.75; H, 7.80; N, 20.20: $C_{15}H_{20}N_4O$ requires C, 66.15; H, 7.40; N, 20.57.

EXAMPLE 10

1-[1-(Indol-3-ylmethyl)piperid-4-yl]-3-benzoylthiourea

Benzoyl chloride (0.49 g, 3.5 mmol) was added to a solution of ammonium thiocyanate (0.29 g, 3.82 mmol) in dry acetone (4 cm$^3$). The reaction mixture was heated under reflux for 10 minutes, then 4-amino-1-(indol-3-ylmethyl)piperidine (0.78 g, 3.41 mmol) was added. The suspension was stirred at room temperature for 1 hour then heated under reflux for 15 minutes and poured into water (20 cm$^3$), precipitating an oil. The supernatant aqueous phase was decanted and the oil triturated with propan-2-ol under reflux to give the title compound as the hydrocyanate salt (0.18 g, 11.7%), m.p. 183°–185° C.

Found: C, 61.39; H, 5.61; N, 15.66%. $C_{22}H_{22}N_4OS \cdot HCNO$ requires C, 61.17; H, 5.58; N, 15.51%.

EXAMPLE 11

3-(3-Methoxybenzoyl)-1-(1-[indol-3-ylmethyl]piperid-4-yl)urea

A solution of formaldehyde (0.4 cm$^3$, 40% aqueous solution) was added to a stirred solution of 1-(3methoxybenzoyl)-3-(piperid-4-yl)urea (1.39 g, 5 mmol) and indole (0.6 g, 5 mmol) in acetic acid (3 cm$^3$). The solution was allowed to stand for 5 hours then diluted with water (50 cm$^3$), basified by addition of ammonia and the precipitated product collected, washed with water, and dried yielding the title compound as the free base (2.1 g). The base was dissolved in hot ethanol (30 cm$^3$), cooled, and acidified with ethanolic hydrogen chloride to precipitate the hydrochloride (2.3 g, 100%). Recrystallisation from aqueous methanol (60% methanol, 70 cm$^3$) gave 1.8 g (81%) m.p. 234°–5° C.

Found: C, 62.75; H, 6.32; N, 12.68. $C_{23}H_{26}N_4O_3 \cdot HCl$ requires C, 62.37; H, 6.14; N, 12.65.

Pharmacological Evaluation

A comparison was made between the preferred compound of the invention, 1-[1-(indol-3-ylmethyl)piperid-4-yl]-3-benzoyl urea (compound I) and one of the preferred compound of U.K. patent specification No. 1,425,354 namely 1-benzoyl-3-[1-(2-[3-indolyl]ethyl)-piperid-4-yl]urea (compound II) which is described in Example 8 of specfication No. 1,425,354. This compound can also be named in an alternative way as 1-[2-([indol-3-yl]ethyl)piperid-4-yl]-3-benzoyl urea.

The results of these tests show that both compounds I and II are potent inhibitors of 5HT uptake but weak inhibitors of noradrenaline uptake. However, in contrast to compound II, compound I does not induce marked CNS depression in animals or significantly reduce the blood pressure of hypertensive rats. In addition compound I does not antagonise the post-synaptic 5HT receptor in vitro.

Inhibition of Noradrenaline and 5-Hydroxytryptamine Uptake in Brain Slices

The effects of test compounds on the neuronal uptake of noradrenaline into slices of cerebral cortex prepared from rat brain is determined according to the method described by Snyder, Green and Hendley, Kinetics of $H^3$-norepihephrine accumulation into slices from different regions of the rat brain (J. Pharm. exp. Therap. 164: 90–102) (1968). The effects of test compounds on the uptake of 5-hydroxytryptamine is obtained in a similar manner except that $H^3$ 5-hydroxytryptamine is used in place of $H^3$ noradrenaline. Concentration-response curves are obtained both for the test compound and for the standard agent, imipramine. The potency of each test compound is expressed in proportion to that of imipramine. Thus, the potency ratio for the test compound =

$$\frac{\text{Molar concentration of imipramine giving 50\% inhibition of }NA\text{ (or }5HT\text{) uptake}}{\text{Molar concentration of test drug giving 50\% inhibition of }NA\text{ (or }5HT\text{) uptake}}$$

Results

| Compound | Potency Ratio (imipramine = 1.0) | |
|---|---|---|
| | Noradrenaline | 5-Hydroxytryptamine |
| II | 0.2 | 8.0 |
| I | 0.06 | 10.0 |

Both compounds are potent inhibitors of 5-hydroxytryptamine uptake and very weak inhibitors of noradrenaline uptake.

Anti-hypertensive activity

Anti-hypertensive activity is determined by the following procedure:

Female rats are rendered hypertensive by unilateral nephrectomy and the s.c. implantation of a pellet containing 30 mg of deoxycorticosterone acetate. The drinking water is replaced by normale saline ad lib for the first four weeks following preparation. Blood pressure stabilise at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solutions of the test compound in 0.5% hydroxypropyl-methyl-cellulose 0.9% saline vehicle. Blood pressures are recorded again at 2, 6 and 24 hours and the results, expressed as a percentage of the pre-dose values compared with those of a similar group of rats receiving vehicle alone.

Results

| Compound | Dose (mg/kg p.o.) | Time(hr) after dosing | BP (% control) | HR (% control) |
|---|---|---|---|---|
| II | 10 | 2 | 64* | 109* |
| | | 6 | 82 | 96 |
| | | 24 | 99 | 97 |
| | 25 | 2 | 49* | 119 |
| | | 6 | 52* | 104 |
| | | 24 | 79* | 97 |

| Compound | Dose (mg/kg p.o.) | Time(hr) after dosing | BP (% control) | HR (% control) |
|---|---|---|---|---|
| | 50 | 2 | 51* | 105 |
| | | 6 | 51* | 90 |
| | | 24 | 62* | 96 |
| I | 50 | 2 | 90 | 101 |
| | | 6 | 102 | 98 |
| | | 24 | 106 | 84 |

*Significantly different from control
BP = systolic blood pressure
HR = heart rate Compound II induced a marked reduction of blood pressure but compound I was without significant activity.

In another procedure for determining anti-hypertensive activity in hypertensive rats, compound II showed marked activity whereas compound I showed moderate activity.

CNS Activity (Effect on Behaviour of Mice)

The test compounds are administered orally to three mice (CF-1 14 to 24 grams) at each of the following doses: 400, 127, 40 and 12.7 mg/kg. The animals are watched for two hours during which time signs of general stimulation (i.e. increased spontaneous motor activity, hyperactivity on tactile stimulation, twitching), general depression (i.e. decreased spontaneous motor activity, decreased respiration) and autonomic activity (i.e. miosis, mydriasis, diarrhoea) are noted.

Results

| Compound | Observation | Lowest Dose (mg/kg p.o.) to induce effect |
|---|---|---|
| II | Decreased activity | 4.0 |
| | Ataxia | 127 |
| | Catalepsy | 400 |
| | Decreased respiration | 400 |
| | Ptosis | 40 |
| I | Decreased activity | 400 |
| | Slight weakness | 400 |

Compound II induced signs of sedation at doses considerably lower than those of compound I required to induce a similar effect.

Motor Activity (Exploratory behaviour in mice)

The test compounds were administered i.p. to mice (3 groups of 4 per dose) at time 0. Seventy minutes later the animals were transferred to square boxes placed beneath the detector heads of Aktograph activity monitors. The exploratory activity of the mice was counted over the following 20 minute period.

Results

| Compound | Dose (mg/kg i.p.) | Exploratory activity score (standard deviation) |
|---|---|---|
| II | 12.5 | 57.3 (14.1) |
| I | 12.5 | 203.3 (16.3) |
| Control | | 265.0 (18.2) |

Compound II caused a marked reduction of exploratory behaviour but compound I was virtually without effect.

5HT Antagonism in Vitro

At $10^{-6}$M, compound II induced a non-competitive blockade of the responses of the isolated rat ileum to 5-hydroxytryptamine. At the same concentration, compound I caused the preparation to relax, but the responses to the subsequent administration of 5HT were not affected.

Further Pharmacological Results

Inhibition of noradrenaline or 5-hydroxytryptamine uptake in brain slices.

| Compound | Potency Ratio (imipramine = 1.0) | |
|---|---|---|
| | Noradrenaline | 5-Hydroxytryptamine |
| Example 2 | inactive | 3.2 |
| Example 3 | 0.19 | 7.8 |
| Example 4 | 0.16 | 0.8 |
| Example 5 | 0.2 | 12.3 |
| Example 6 | 0.06 | 5.0 |
| Example 7 | 0.19 | 7.8 |
| Example 8 | 0.1 | 1.04 |
| Example 10 | — | 6.5 |
| Example 11 | — | 2.7 |

The invention includes a method of alleviating depression in a warm blooded animal afflicted with depression, which method comprises administering to said animal an effective amount of a compound of formula II as defined above (wherein $R^5$, $R^6$ and $R^7$ are as defined above).

The amount of compound used will depend on the compound employed, the severity and nature of the depression and the animal being treated. With large animals (about 70 kg body weight) by the oral route the dose is from about 5 to about 75 mg and preferably from about 10 to about 25 mg every four hours or as needed. By the parenteral route the dosage is from about 2 to about 35 mg as needed. Ideally therapy should be initiated with lower dosages, the dosage thereafter being increased until the desired anti-depressive effect is obtained.

The most preferred compound for use in the method of the invention is 1-[1-(indol-3-ylmethyl)piperid-4-yl]-3-benzoyl urea and its pharmaceutically acceptable acid addition salts. Other preferred compounds are 1-[1-(indol-3-ylmethyl)piperid-4-yl]-3-(2-thenoyl) urea; 1-benzoyl-3-[1-([5-hydroxyindol-3-yl]methyl)piperid-4-yl]urea; 1-[1-(indol-3-ylmethyl)piperid-4-yl]-3-benzoyl-thiourea and their pharmaceutically acceptable acid addition salts.

We claim:

1. A method of alleviating depression in a warm blooded animal afflicted with depression which method comprises administering to said animal an effective anti-depressant amount of a compound of formula II,

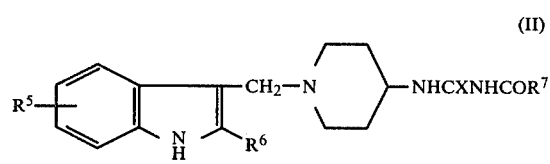
(II)

or a pharmaceutically acceptable acid addition or quaternary ammonium salt thereof wherein $R^5$ represents hydrogen, hydroxy, lower alkoxy or lower alkyl, $R^6$ represents hydrogen or lower alkyl, and $R^7$ represents phenyl, lower alkoxy phenyl, halophenyl, or thenyl and X represents oxygen or sulphur.

2. A method as claimed in claim 1, wherein the compound of formula II is 1-[1-(indol-3-ylmethyl)piperid-4-yl]-3-benzoyl urea or a pharmaceutically acceptable acid addition salt thereof.

3. A method as claimed in claim 1, wherein the compound of formula II is 1-[1-(indol-3-ylmethyl)piperid-4-yl]-3-(2-thenoyl)urea or a pharmaceutically acceptable acid addition salt thereof.

4. A method as claimed in claim 1, wherein the compound of formula II is 1-benzoyl-3-[1-([5-hydroxyindol-3-yl]methyl)piperid-4-yl]urea or a pharmaceutically acceptable acid addition salt thereof.

5. A method as claimed in claim 1, wherein the compound of formula II is 1-[1-(indol-3-ylmethyl)piperid-4-yl]-3-benzoylthiourea or a pharmaceutically acceptable acid addition salt thereof.

* * * * *

UNITED STATES PATENT AND TRADEMARK OFFICE
CERTIFICATE OF CORRECTION

PATENT NO. : 4,209,521
DATED : June 24, 1980
INVENTOR(S) : J. L. Archibald et al It is certified that error appears in the above-identified patent and that said Letters Patent are hereby corrected as shown below:

The Abstract, line 5 below the formula should read — thienyl - for "thenyl";

Column 1, line 59 should read — thienyl — for "thenyl";

Column 3, line 66 should read — formulation — for "formation";

Column 5, line 10 should read — $C_{23}H_{26}N_4O_2HCl$ — for "$C_{23}H_{26}N_4HCl$";

Column 6, line 32 should read — thienyl — for "thenyl";
line 35 should read — thienyl — for "thenyl";

Column 7, line 32 should read — $C_{22}H_{24}N_4OS$ — for "$C_{22}H_{22}N_4OS$";
line 58 should read — compounds — for "compound";

Column 8, line 11 should read — norepinephrine — for "norepihephrine";
line 47 should read — normal — for "normale".

Claim 1, penultimate line, should read — thienyl — for "thenyl".

Signed and Sealed this

Twenty-fourth Day of March 1981

[SEAL]

Attest:

RENE D. TEGTMEYER

Attesting Officer

Acting Commissioner of Patents and Trademai